United States Patent [19]

Audeh et al.

[11] Patent Number: 5,354,938
[45] Date of Patent: Oct. 11, 1994

[54] MODIFICATION OF SURFACE PROPERTIES OF HYDROGEN FLUORIDE

[75] Inventors: Costandi A. Audeh, Princeton; Saverio G. Greco, Princeton Junction, both of N.J.

[73] Assignee: Mobil Oil Corporation, Fairfax, Va.

[21] Appl. No.: 719,275

[22] Filed: Jun. 21, 1991

[51] Int. Cl.$^5$ ................................. C07C 2/60
[52] U.S. Cl. ...................... 585/724; 585/710; 502/150; 502/168; 423/265
[58] Field of Search ............... 423/265, 483; 585/710, 585/724; 502/168, 150

[56] References Cited

U.S. PATENT DOCUMENTS

| | | | |
|---|---|---|---|
| 3,766,293 | 10/1973 | Parker et al. | 585/724 |
| 3,778,489 | 12/1973 | Parker et al. | 260/683.43 |
| 4,357,481 | 11/1982 | Kramer | 585/724 |
| 4,938,935 | 7/1990 | Audeh et al. | 423/240 |
| 5,202,518 | 4/1993 | Del Rossi | 585/724 |

*Primary Examiner*—Gary P. Straub
*Assistant Examiner*—Stuart L. Hendrickson
*Attorney, Agent, or Firm*—A. J. McKillop; M. D. Keen

[57] ABSTRACT

The surface properties of hydrofluoric acid are modified by the addition of a perfluoro compound in order to reduce the tendency of the HF to form an aerosol upon any release of HF alkylation acid from an HF alkylation unit. The perfluoro compounds which are used are the perfluorosulfonic acid fluorides and perfluorocarboxylic acid fluorides.

8 Claims, No Drawings

MODIFICATION OF SURFACE PROPERTIES OF HYDROGEN FLUORIDE

FIELD OF THE INVENTION

This invention relates to a method for the modification of the surface properties of hydrogen fluoride with the objective of mitigating the hazards of aerosol formation if hydrogen fluoride vapors are released from a process unit in the event of an accidental release of the unit contents.

BACKGROUND OF THE INVENTION

Hydrogen fluoride, or hydrofluoric acid (HF) is used as a catalyst in isomerization, condensation, polymerization and hydrolysis reactions. The petroleum industry uses anhydrous hydrogen fluoride primarily as a liquid catalyst for alkylation of olefinic hydrocarbons to produce alkylate for increasing the octane number of gasoline and the HF alkylation process is responsible for producing a significant proportion of high octane gasoline components in the United States at the present time. In 1984, for example, the total U.S. HF alkylation capacity was 69,160 $m^3$ (435,000 barrels) per day, using about 0.43 to 1.0 kg of HF per cubic meter of alkylate. In spite of the corrosive and toxic nature of hydrogen fluoride, the superior design, construction and operational precautions accumulated over years of experience in its manufacture and use have shown that HF can be handled safely, provided that its hazards are recognized and appropriate precautions taken. Although many safety precautions are taken there remains a concern for the potential danger of leaks.

An HF-alkylation acid composition is composed of about 88% HF, 6.5% acid soluble oils, 4% C3/C4 alkylate and 1.5% water. Generally, an alkylating plant is able to cope with minor spills of HF-alkylation acid caused by mechanical failures or corrosion, but in the unlikely event of a massive leak or spill of HF-alkylation acid from an alkylating unit, an aerosol cloud may form instantaneously. It is estimated that the cloud will be made up of 70 to 88% of HF aerosol droplets having a size in the range of 0.1 to 1.0$\mu$ and a surface tension of 8.62 dynes/cm at 18.2° C. These droplets are very small compared to the droplets of water in a normal water drench and therefore a water drench requires large amounts of water for removing the acid spill.

Variables that control the size of droplets in a cloud include the charge on the particles, the surface tension of the liquid from which the particles are made, the influence of various solutes present in the HF-alkylation acid mixture as well as the mechanism of creating the aerosol droplets. Thus, the alkylation acid on escape will develop a cloud characteristic of its composition, the charge and size of the HF droplets and the surface tension of the droplets at the time of the leak.

A number of alternative methods to the simple water drench have been proposed. U.S. Pat. No. 4,210,460, for example, describes a method for treating an HF liquid spill by applying a quantity of an aqueous solution of calcium acetate to the spill in an amount equal to at least seven times the estimated volume of the spill, after which the spill is treated with powdered magnesium oxide and a pH indicator such as bromothymol blue. After the mixture reaches a persistent blue color, indicating a safe state, the spill is cleaned up mechanically.

At the 1982 Hazardous Material Spills Conference, Edward C. Norman of National Foam System Inc. reported the application of CHF-784 foam (a proprietary composition) to the contents of a damaged tank emitting an HF cloud after treatment with limestone. An immediate reduction in fume evolution was apparent after the foam application.

Gordon K. Braley, at the proceedings of the 1980 National Conference on Control of Hazardous Material Spills, in Louisville, Ky. on May 15, 1980 reported the treatment of relatively small amounts of controlled liquid spills of anhydrous hydrogen fluoride with high molecular weight polymers including polyacrylamide, polymethylmethacrylate, and polyvinyl alcohol. These materials applied in the form of a bead polymer formed a "skin" over the spill preventing fuming of the liquid. Polyacrylamide was deemed the most effective skin-forming agent.

Of the art cited above, only Edward C. Norman discusses an alleged successful treatment of a cloud containing HF. However, the composition used to treat such a cloud was not publicly disclosed.

U.S. Pat. No. 4,938,935 discloses a practical technique for altering or modifying the properties of the HF vapor cloud in order to make it more susceptible to knock-down by a water drench. According to the technique described in this patent, a proton acceptor which has multiple sites available for protonation is brought into contact with the HF acid to form multiply charged, highly polar species which modify the nature of the acid cloud and render it amenable to being treated with a water drench. The additive i.e. the proton acceptor, may be added to the alkylation acid as a permanent component of the inventory of acid or, alternatively, it may be added to the alkylation acid when necessary in the event of a release of acid from the unit.

U.S. Pat. No. 4,938,936 discloses a method of mitigating the effects of an HF leakage from a process unit by the use of a fighting agent such as sodium carbonate which generates a foam on contact with the acid and which also acts to neutralize the acid. The foam may be stabilized by the addition of surfactants and foam-forming agents such as hydrolyzed proteinaceous materials.

One problem encountered with the use of compounds which are added to the permanent inventory of alkylation acid, as distinct from being added when they are needed in the event of an emergency, is that they may react with the HF or be destroyed by it. Reaction products may interfere with the alkylation reaction and a total destruction of the additive will, of course, eliminate its utility for the desired purpose.

SUMMARY OF THE INVENTION

We propose the use of perfluorinated compounds as additives for addition to the hydrofluoric acid in an HF alkylation unit. These additives may be used to modify the properties of the acid to suppress or inhibit the formation of an aerosol cloud in the event of a release of HF alkylation acid from an alkylation unit or, alternatively, may be used to modify its properties so that any aerosol that may be formed in an uncontrolled release is more susceptible to knock-down by water, in the manner described in U.S. Pat. No. 4,938,935.

The perfluorinated compounds which we propose to use are the fluorides of perfluorosulfonic and perfluorocarboxylic acids. These derivatives will not be influenced chemically by the hydrogen fluoride because the functional group is a fluorine derivative and the carbon chain is already perfluorinated. Any interaction with the alkylating agent will result in the exchange of one fluorine atom for another and if the fluoride is hydrolyzed, it will produce HF which is the alkylating agent.

DETAILED DESCRIPTION

Two types of HF alkylation unit are in general use at the present time. In one type, the gravity flow type reactor, the hydrocarbon reactants meet the liquid hydrofluoric acid entering the bottom of the reactor from an acid cooler to which the acid flows from an acid settler after the alkylation reaction has taken place. The driving force for the circulation of the acid and the hydrocarbon reactants is the difference in density between the catalyst and the hydrocarbons at different points in the system plus the jetting action of the hydrocarbon injection nozzles. The acid settler permits a phase separation to take place between the denser acid phase and the lighter hydrocarbon phase and the acid phase is recycled to the acid cooler and then back to the reactor; the hydrocarbon phase including the alkylation product is fed to a fractionation section where the propane and unreacted isobutane are separated from the motor fuel alkylate fraction. The isobutane is recycled and propane is removed from the unit. A unit of this type is described in U.S. Pat. No. 3,716,343, to which reference is made for a description of the unit and its mode of operation.

The other principal type of unit currently in use is the pumped flow type in which the mixed hydrocarbon feed is introduced into the reactor through spargers along the vertical length of the reactor. From the reactor the catalyst and the hydrocarbons flow into an acid settler where a phase separation takes place in the same way as in the gravity flow unit, permitting product and catalyst recovery in the same manner as described above. Compared to the gravity flow reactor, the pumped circulation reactor uses a smaller inventory of acid because of the higher circulation speed of the catalyst in this type of unit.

According to the present invention, the additive which is used to modify the properties of the HF alkylation acid so as to suppress or inhibit the formation of an aerosol cloud upon any release of the acid from the alkylation unit is a perfluorosulfonic fluoride or a perfluorocarboxylic acid fluoride, or a combination of the two. These derivatives will not be influenced chemically by the hydrogen fluoride because the functional group is a fluorine derivative and the carbon chain is already perfluorinated. Any interaction with the alkylating agent will result in the exchange of one fluorine atom for another and if the fluoride is hydrolyzed, it will produce HF which is the alkylating agent.

The perfluorosulfonic acid fluorides are represented by the formula:

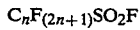

$$C_nF_{(2n+1)}SO_2F$$

and the perfluorocarboxylic acid fluorides by the formula:

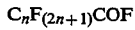

$$C_nF_{(2n+1)}COF$$

where n is typically from 1 to 20 and usually is at least 2 up to 18, and preferably at least 4 up to about 12. A typical perfluoro compound of this type is perfluoroheptanyl fluoride, $C_6F_{13}CFO$.

The perfluoro compound is chosen for its effect on the surface tension of the HF alkylating acid, so that the surface tension is changed to the point that the acid does not form an aerosol upon any release from the unit.

The exact amount of added perfluoro compound acid will typically be in the range of 0.01 to 30 weight percent relative to the HF in the unit. Normally, however, amounts of from about 1 to 20 weight percent, preferably from about 2 to 5 weight percent of the acid in the unit will be used. If the additive is added to the HF acid when an emergency condition arises, for example, by the additive dispensing system disclosed in U.S. Pat. No. 4,938,935 or Ser. No. 07/489,986, it is suitably added in similar amounts, although more may be tolerated since there is then no concern with interference with the alkylation reactions.

Because of the lack of reactivity of the additive with the alkylating acid, the perfluoro compound may be added directly to the HF acid circulating in the alkylation unit. Alternatively, it may be injected or dispensed into the acid in the event of an emergency condition arising. If the perfluoro compound is not mixed with the acid on a permanent basis, it may be stored separately from the acid in a storage vessel or container and then injected into the circulating inventory of acid when the need arises. In this case, the alkylation unit will usefully incorporate features which enable the additive to be injected into the acid whenever needed to change the characteristics of the acid so that upon release into the atmosphere the physical properties of the acid have been altered, thus reducing the hazard presented by the released acid. A preferred form of the alkylation unit for adding or dispensing the additive into the acid in the unit is described in Ser. No. 07/489,986, where phosphoric acid is used as the additive. The same type of unit may be used with the perfluoro compounds as the additive. In this type of unit, the additive is maintained in a pressurized container in the unit and is connected to the reaction section of the unit by means of additive release valves under the control of an emergency controller which opens the valves and permits the additive to enter the reaction section of the unit and mix with the acid to modify its characteristics. The container may be connected to the major acid-containing process vessels in the unit, specifically the acid settler and the acid cooler (in a gravity flow unit) or the acid settler and the reactor (in a pump-around unit) in order to bring the additive into contact with the bulk of the acid in the unit in the shortest possible time, so as to modify its properties as quickly as possible. Reference is made to Ser. No. 07/489,986 for a disclosure of the modified HF alkylation unit.

The acid modification can be practised in combination with other methods for removing or dealing with HF, for example, as described in U.S. Pat. Nos. 4,938,935 and 4,938,936, a particularly effective method for handling the HF release utilizes a tripartite chemical drench system which includes an initial water drench.

We claim:

1. A method for modifying the properties of an acid catalyst comprising liquid hydrofluoric acid to mitigate the effects of an aerosol formation upon release of the acid from a process unit containing the acid, which comprises adding to the hydrofluoric acid a perfluoro compound selected from the group consisting of pefluorosulfonic acid fluorides and perfluorocarboxylic acid fluorides.

2. A method according to claim 1 in which the perfluoro compound is added to the HF acid in an amount sufficient to change the character of hydrofluoric acid droplets formed upon release, to render the droplets in the aerosol more susceptible to knock-down by a water drench.

3. A method according to claim 1 in which the amount of perfluoro compound is from 1 to 30 weight percent relative to the HF.

4. A method according to claim 1 in which the amount of perfluoro compound is from 2 to 10 weight percent relative to the HF.

5. In an HF alkylation process in which an iso-paraffin is alkylated in an HF alkylation unit with an olefin in the presence of a liquid alkylation catalyst comprising liquid hydrofluoric acid alkylation catalyst to produce an iso-paraffinic, gasoline boiling range alkylation product, the improvement comprising modifying the properties of the liquid alkylation catalyst in the alkylation unit to mitigate the effects of the formation of an aerosol upon release of the acid from the alkylation unit, which comprises adding to the alkylation catalyst a perfluoro compound selected from the group consisting of perfluorosulfonic acid fluorides and perfluorocaboxylic acid fluorides.

6. A method according to claim 5 in which the perfluoro compound is added to the HF acid in an amount sufficient to change the character of hydrofluoric acid droplets formed upon release, to render the droplets in the aerosol more susceptible to knock-down by a water drench.

7. A method according to claim 5 in which the amount of perfluoro compound is from 1 to 30 weight percent relative to the HF.

8. A method according to claim 5 in which the amount of perfluoro compound is from 2 to 10 weight percent relative to the HF.

* * * * *